(12) United States Patent
Da Silva et al.

(10) Patent No.: US 10,383,909 B2
(45) Date of Patent: Aug. 20, 2019

(54) USE OF A PLANT EXTRACT, PHARMACEUTICAL COMPOSITIONS AND USE THEREOF

(75) Inventors: Avaniel Marinho Da Silva, Recife-PE (BR); Tulio Flavio Accioly Lima E Moura, Natal-RN (BR); Severno Barbosa Dos Santos, Recife-PE (BR)

(73) Assignee: HEBRON FARMACEUTICA PESQUISA, DESENVOLVIMENTO E INOVACAO TECNOLOGICA LTDA, Santana do Parnaiba (BR)

( * ) Notice: Subject to any disclaimer, the term of this patent is extended or adjusted under 35 U.S.C. 154(b) by 151 days.

(21) Appl. No.: 13/816,469

(22) PCT Filed: Aug. 3, 2011

(86) PCT No.: PCT/BR2011/000259
§ 371 (c)(1),
(2), (4) Date: Apr. 29, 2013

(87) PCT Pub. No.: WO2012/019255
PCT Pub. Date: Feb. 16, 2012

(65) Prior Publication Data
US 2013/0302419 A1 Nov. 14, 2013

(30) Foreign Application Priority Data
Aug. 11, 2010 (BR) .............................. PI1002720-3

(51) Int. Cl.
A61K 36/22 (2006.01)
A61K 36/77 (2006.01)

(52) U.S. Cl.
CPC .............. *A61K 36/77* (2013.01); *A61K 36/22* (2013.01)

(58) Field of Classification Search
CPC ................................ A61K 36/22; A61K 36/77
See application file for complete search history.

(56) References Cited

U.S. PATENT DOCUMENTS

| 8,652,536 B2* | 2/2014 | da Luz Moreira et al. ... 424/725 |
| 8,658,567 B2* | 2/2014 | Su et al. ........................ 504/189 |
| 2004/0151769 A1* | 8/2004 | Esperester et al. ............ 424/465 |
| 2006/0108739 A1* | 5/2006 | Lutz .............................. 273/292 |

FOREIGN PATENT DOCUMENTS

BR P10705252-9 A2 1/2009

OTHER PUBLICATIONS

CArlini et al. Antiulcer Effect of the Pepper Trees Chinus Terebinthifolius Raddi (Aroeria-Da-Praia) and Myracrodruon Urundeuva Allemao, Anacardiaceae (Aroeira-Do-Sertao), Brazilian Journal of Pharmacognosy 20(2): 140-146, Apr./May 2010, pp.*
Santos et al. GED: Gastroenterologia Endoscopia Digestiva 29(4):118-125, Apr. 2010 as cited in the Written Opinion of the International Searching Authority (ISA).*
ACS Carvalho; MM Guedes; AL. de Souza; MTS Trevisan; AF Lima; FA Santos; VSN Rao "Gastroprotective Effect of Mangiferin, a Xanthonoid from Mangifera indica, against Gastric Injury Induced by Ethanol and Indomethacin in Rodents" Planta Med,2007 (epub. Oct. 4, 2007), 73(13),pp. 1372-1376. DOI: 10.1055/s-2007-990231.*
A Luiz-Ferreira, et al ("Mechanisms of the gastric antiulcerogenic activity of Anacardium humile St. Hil. on ethanol-induced acute gastric mucosal injury in rats" Molecules,2010, 15,pp. 7153-7166. DOI: 10.3390/molecules15107153.*
Carlini EA; Duarte-Almeida JM; Tabach R "Assessment of the toxicity of the Brazilian pepper trees Schinus terebinthifolius Raddi (Aroeira-da-praia) and Myracrodruon urundeuva Allemão (Aroeira-do-sertão)" Phytother Res, May 2013 (Epub Jul. 4, 2012), 27(5), pp. 692-698. doi: 10.1002/ptr.4767. (Year: 2012).*
Novaes, RD et al "Ethnopharmacology as Current Strategy in the Search of Novel Anti-Ulcerogenic Drugs: Case of a Brazilian Medicinal Plant (Maytenus ilicifolia Mart. ex. Reiss" Peptic Ulcer Disease (Chai, Jianyuan Ed.), Nov. 4, 2011, chapter 20, pp. 374-400. ISBN 978-953-307-976-9. (Year: 2011).*
dos Santos OJ, et al "Evaluation of the Aroeira (Schinus terebinthifolius Raddi</i>) extract on the healing process of gastroraphy in rats" Acta Cirorgica Brasileira, 2006, vol. 21 (Suppl.2), pp. 39-45. (Year: 2006).*
Severino Barbosa Dos Santos et al., "Comparação da eficácia da aroeira oral (*Schinus terebinthifolius* Raddi) com omeprazol em pacientes corn gastrite e sintomas dispépticos: estudo randomizado e duplo-cego," GED Gastroenterologia E Endoscopia Digestiva, vol. 29, No. 4, pp. 118-125, Dec. 2010.
Severino Barbosa Dos Santos et al., "Comparaçõda eficácia da aroeira oral (*Schinus terebinthifolius* Raddi) com omeprazol em pacientes com gastrite e sintomas dispépticos: estudo randomizado e duplo-cego," GED Gastroenterologia E Endoscopia Digestiva, vol. 29, No. 4, pp. 118-125, Abril de 2010.
Elisaldo A. Carlini et al., Antiulcer effect of the pepper trees *Schinus terebinthifolius* Raddi (aroeira-da-praia) and *Myracrodruon urundeuva* Allemão, Anacardiaceae (aroeira-do-sertão), Brazilian Journal of Pharmacognósy, vol. 20, No. 2, pp. 140-146, Mai de 2010.
A.M.S. Menezes et al., "Anti-ulcerogenic Activity of *Astronium urundeuva*," Fitoterapia, vol. 57, No, 4, pp. 253-256 (1986).
V.S. Rao et al., "Studies on the Anti-Ulcerogenic Activity of *Astronium urundeuva* Engl. II Aqueous Extract," Brazilian Journal of Medical and Biological Research, vol. 20, No. 6, pp. 803-805 (1987).

(Continued)

*Primary Examiner* — Aaron J Kosar
(74) *Attorney, Agent, or Firm* — Arent Fox, LLP (57) ABSTRACT

The present invention relates to the use of a plant extract obtained from at least one plant of the Anacardiaceae family, for the preparation of a pharmaceutical composition used as a new herbal medicine for the prophylaxis and/or treatment of disorders associated with the digestive tract, and the relief of symptoms associated with these disorders. Additionally, through the scope of the present invention, the substances isolated from said extract also consist of the active ingredients of pharmaceutical compositions. A third objective of the invention is the use of said pharmaceutical compositions in the preparation of the class of herbal medicines for the prophylaxis and/or treatment of disorders associated with the digestive tract, in different stages, with posology and daily dosing.

17 Claims, 3 Drawing Sheets

(56) References Cited

OTHER PUBLICATIONS

Lic. Maria Julia Martinez et al., "Actividad Antimicrobiana del *Schinus terebenthifolius* Raddi (Copal)," Rev. Cubana Plant Med, vol. 1, No. 3, pp. 37-39 (1996).

A.M.S. Menezes et al., "Effect of *Astronium Urundeuva* (Aroeira) on Gastrointestinal Transit in Mice," Brazilian Journal of Medical and Biological Research, vol. 21, No. 3, pp. 531-533 (1988).

\* cited by examiner

FIGURE 6 ns consist of:

USE OF A PLANT EXTRACT, PHARMACEUTICAL COMPOSITIONS AND USE THEREOF

CROSS-REFERENCED TO RELATED APPLICATIONS

This application is a National Stage entry of International Application PCT/BR2011/000259 filed Aug. 3, 2011, which claims priority to Brazilian Application No. PI1002720-3, filed Aug. 11, 2010.

FIELD OF THE INVENTION

The present invention relates to the use of a plant extract obtained from at least one plant of the Anacardiaceae family, in a pharmaceutical composition used in the preparation of a novel herbal medicine. Additionally, the present invention further comprises pharmaceutical compositions comprising at least one substance isolated from said extract. A third objective of this invention is the use of said pharmaceutical compositions in the preparation of the class of herbal medicines for the prophylaxis and/or treatment of disorders associated with the digestive tract, in different stages, with posology and daily dosing.

BACKGROUND

Medicinal plants are proven sources of natural products with therapeutic activity. Medicinal plants have, in their compositions, different compounds to cure various ills affecting the health of humans and animals. Said plants have at least one active ingredient responsible for the curative effect, in addition to their phytocomplex effect.

However, despite the use of these ancient plants for the treatment of human and animal diseases, they are most often used empirically, i.e. without scientific basis, and with only the foundation of knowledge of popular wisdom.

However, due to lack of scientific information about their uses, it is known that such plants with medicinal properties can be wrongly applied, since many of them have toxic principles which may cause serious problems associated with indiscriminate use.

Over the past decades, the medical and pharmaceutical sciences have invested efforts to prove the efficacy propagated of medicinally plants in the treatment of simple diseases, as well as more complex diseases, such as those from various types of cancer.

In northeastern Brazil, the population makes empirical use of medicinal plants through teas, extracts, poultices, ash and other forms of "preparations" for "medicinal" use.

With respect to such use, we exemplify some plants and some of their respective uses: rosemary tea, used as a sedative and to treat respiratory problems; tea or arruma bath for cramps and eye problems; teas and herb baths of Santa Maria as a vermifuge and for the treatment of wounds; among a myriad of other plants used for medicinal purposes.

Within this arsenal of medicinal plants, is the aroeira, or aroeiraBeach Aroeira, as it is popularly known, which is a plant of the species *Schinus terebinthifolius* Raddi; a mid-sized plant belonging to the Anacardiaceae family.

In general, the use of such popular plant species shows evidence of their efficacy in the treatment of inflammatory, infectious and healing processes.

It is known that the popular use of Aroeira consists basically in the selection of the stem bark as the main part of the plant used in homemade preparations. Such preparations consist of:

1) bark tea to wash locations of cuts and bruises, helping in the healing of scars;
2) infusions of barks, orally administered, used in the treatment of inflammation such as inflammation of the uterus;
3) poultice, which is prepared with boiled bark, in the form of a "paste," which can replaces plaster for fractures;
4) leathery bark tanned in a container with water, for a few hours, in which the strained solution is used for gargles and throat infections;
5) powder from scraped bark, called powder, used for snake bites.

As already noted, due to the fact that these forms of use are uncontrolled, wherein the amounts employed are not well established, the information may cause both benefit as well as adverse results.

Specifically, with respect to Aroeira, the selection of leaves, flowers, fruits, peels, cores and the essential oils of *S. terebinthifolius* for such uses as in herbal medicines has been the subject of constant studies regarding its toxicological and pharmacological properties, and about its chemical constituents from ethanol, essential oils and aqueous extracts.

In this sense, the phytochemical research of essential oils extracted from the leaves of *S. terebinthifolius* showed that are present dozens of substances from the class of terpenoids—volatile substances having the characteristic bouquet of fragrances of flowers, fruits and leaves of *S. terebinthifolius*.

The more polar alcoholic and aqueous extracts obtained from the stem bark contain a large number of different classes of substances, particularly phenols, tannins, chalcones, flavonoids and terpenes.

However, those knowledgeable in the art know that in the phytochemical processes of extraction, depending on the solvent used in the extraction step of a given part of a plant or, for the same solvent, changing the temperature used in the extraction process, completely changes the composition of chemical constituents. More specifically, the concentration of substances in a composition depends on the conditions employed in the step of obtaining extracts, such that the ethanolic extract and methanol extract differ from that of the aqueous extract.

It is well established in phytochemistry that in these processes, along with variants (solvent and temperature), the extraction time can also provide different extraction products, of different compositions, which, for use as medicine, are vital in providing the main toxicological activities and therapeutic properties and indication of use of the medicine.

The literature reveals that the tannin is the most researched chemical constituent of the plant species *S. terebinthifolius*, due to its high concentration in the species, and also due to its related biological activities.

The aqueous and alcoholic extracts obtained from the fruits of *S. terebinthifolius*, are rich in substances from the class of tannins, and exhibit differentiated antimicrobial activities, due in part to different concentrations of their constituents.

Beyond these properties, the aqueous extracts of the stem bark exhibit anti-inflammatory and healing properties in different laboratory models of pharmacological evaluation, such as wounds, burns and ulcers. The principle active from the bark is used as a styptic, febrifuge and depurative, in addition to acting in wound healing, treating leucorrhoeas and as a mouthwash for ulcers and gingivitis.

Regarding the prior art, the healing activity is described in document PI0605952-0. The referred document describes a biopharmaceutical wound healing of diabetic, or non-diabetic patients for mycoses, whitlow, rashes, burns etc. It is an herbal product containing extracts of four Brazilian plants (*Schinus terebinthifolius* Raddi, *Physalis angulata* Linné, *Cereus hildemanianus* Shucus and *Anadenanthera colubrina* Benth).

The terebinthona, and various other substances present in the extract of *S. terebinthifolius*, also have antimicrobial activity, such as hydroxymasticadienoic, ursolic and terebinthifolic acids.

The antimicrobial activity of terebinthona has been demonstrated in the art, in vitro, against *Klebsiella pneumoniae, Alcaligenes faecalis, Pseudomonas aeruginosa, Leuconostoc cremoris, Enterobacter aerogenes, Proteus vulgaris, Clostridium sporogenes, Acinetobacter calcoacetica, Escherichia coli, Beneckea natriegens, Citrobacter freundii, Serratia marcescens, Bacillus subtilis, Staphylococcus aureus* and various species of fungi (*Aspergillus*).

The decoction of the stem bark of the Beach Aroeira has traditionally been used to treat genital discharge and cervicitis. Multiple mechanisms of action have been described for the action of this extract which has demonstrated itself as an anti-inflammatory non-steroidal, due to the specific competitive inhibition of phospholipase A2, whose active ingredients are assigned to two of its components, schinol and masticadienoic acid.

In document PI 9905205-9, the use of an aqueous extract of Aroeira is described in the preparation of pharmaceutical compositions in the form of tinctures, emulsions (ointments, creams or gels) for treating inflammation of the vaginal tract. Said extract can be used in the pharmaceutical composition either in its pure natural form, or associated with other synthesized forms.

However, for all the teachings from popular knowledge, even when added to the currently obtained results of pharmacological and microbiological research, we note that the technique lacks an herbal medicine providing efficient action against dyspeptic symptoms; disturbances that affect the digestive tract.

Discomfort of the digestive tract comprises highly prevalent pathologies in the world population, with the primary etiologic agent being the bacterium *Helicobacter pylori*. It is estimated that about 60-70% of the world population are carriers of the bacteria and present with gastroduodenal disease activity.

Currently, the global pharmaceutical market has synthetic drugs with anti *H. pylori* action, such as the antibiotics amoxicillin and clarithromycin, associated with proton pump inhibitors, with potential adverse effects.

In the treatment of complaints related to peptic ulcer, gastritis, duodenitis and gastropathies, proton pump inhibitors are habitually used, with the prototype being the active ingredient Omeprazole, as the synthetic drug reference.

In a second option of medication for alleviation and treatment of disturbances of the digestive tract, the technique comprises the use H-2 histamine receptor blockers, such as ranitidine and cimetidine. However, these drugs have potential adverse effects for patients.

In order to provide an alternative technique in the treatment of gastric mucosal lesions, an inexpensive alternative herbal medicine therapy accessible to the population, was developed from hydroalcoholic extract of Aroeira, indicated as a specific use in the treatment of disorders of the digestive tract such as peptic ulcer, gastritis, duodenitis and gastropathies. The present invention was thus developed.

SUMMARY OF THE INVENTION

The present invention relates to the use of a plant extract obtained from at least one plant of the Anacardiaceae family, in a pharmaceutical composition used in the preparation of a new herbal medicine for prophylaxis and/or treatment of disorders associated with the digestive tract. Preferably, the plant species of the Anacardiaceae family may be selected from the genus *Schinus*. Even more preferably, the plant species selected for extraction is *Schinus terebinthifolius*. The above crude hydroalcoholic extract of *Schinus terebinthifolius* is used as the active ingredient in a pharmaceutical composition for treating disorders of the digestive tract. Additionally, although still within the scope of the present invention, the isolated substances of the referred said extract *Schinus terebinthifolius* also consist of the principle active ingredient of pharmaceutical compositions which are now objects of the present invention herein. A third objective of the invention is the use of said pharmaceutical compositions in the preparation of the class of herbal medicines for the prophylaxis and/or treatment of disorders associated with the digestive tract, in different stages, with posology and daily dosing.

DETAILED DESCRIPTION OF THE INVENTION

The present invention relates to the use of a plant extract obtained from plants of the Anacardiaceae family, in a pharmaceutical composition used in the preparation of a novel herbal medicine.

More specifically, the plant extract is obtained by extraction reactions conducted with polar organic solvents and water.

Preferably, the plant species of the Anacardiaceae family can be selected among the species of the genus *Schinus* or *Myracrodruon*, currently known by botanists as *Astronium*.

More particularly, these species can be selected among the species: *Schinus andinus, Schinus angustifolius, Schinus antiarthriticus, Schinus areira, Schinus bituminosus, Schinus bonplandianus, Schinus brasiliensis, Schinus bume-*

*lioides, Schinus cabrerae, Schinus chebataroffi, Schinus chichita, Schinus crenatus, Schinus dentatus, Schinus dependens, Schinus discolor, Schinus diversifolius, Schinus engleri, Schinus fagara, Schinus fasciculatus, Schinus ferox, Schinus gracilipes, Schinus huigan, Schinus huygan, Schinus indicus, Schinus johnstonii, Schinus kauselii, Schinus latifolius, Schinus lentiscifolius, Schinus leucocarpus, Schinus limonia, Schinus longifolius, Schinus marchandii, Schinus maurioides, Schinus mellisii, Schinus meyeri, Schinus microphyllus, Schinus molle, Schinus molleoides, Schinus montanus, Schinus mucronulatus, Schinus myricoides, Schinus myrtifolius, Schinus occidentalis, Schinus odonellii, Schinus paraguariensis, Schinus patagonicus, Schinus pearcei, Schinus piliferus, Schinus polygamus, Schinus praecox, Schinus pubescens, Schinus ramboi, Schinus resinosus, Schinus rhoifolius, Schinus roigii, Schinus sinuatus, Schinus spinosus, Schinus tenuifolius, Schinus terebinthifolius, Schinus ternifolia, Schinus tomentosa, Schinus tragodes, Schinus velutinus, Schinus venturii* and *Schinus weinmannifolius.*

In addition, the plant species of the Anacardiaceae family may also be selected from the species *Astronium urundeuva* (*Myracrodruon urundeuva*), *Astronium graveolens* and *Astronium juglandifolium*. Specifically, for the present invention, the species that sometimes can also be preferably used is *Astronium urundeuva*, also popularly known as Field Aroeira and Sierra Aroeira or Backwoods Aroeira.

More specifically, in the present embodiment, the specie of *Schinus* selected to be used for extraction of said extract is *Schinus terebinthifolius*.

That species has several synonyms, such as: Linnaeus Soft *Schinus*, Soft *Schinus aroeira* and *Schinus mucromulata* Mart, and is also popularly known as Beach Aroeira, Paraná Aroeira Aroeira Pimenteira, Aroeira Mansa and Red Aroeira. The name depends on the region where it is found.

Due to the gastric cytoprotective effect of the active substances of dry extract of *Schinus terebinthifolius* Raddi it is possible by means of the present invention, to aggregate a currently known technique for one more possibility of using this extract.

The dry extract of *Schinus terebinthifolius* Raddi has, among its constituents, biflavonoid substances, i.e. dimers which are precursors of tannins. These substances exhibit high anti-inflammatory action and are responsible for the effects of the herbal medicine now developed.

For the present invention, the crude extract of *Schinus terebinthifolius* Raddi is achieved by means of new technological processes using specific parts of plant species such as the stem bark in order to enable a higher product yield. Note that, although the stem barks are the preferred sources, said extract may also be extracted from other plant parts such as leaves, flowers, and fruits and so on.

For the extraction process described herein, an organic substance is used as the extraction solvent in defined proportions. For the present invention, the organic solvent used is selected from hydrocarbon derivatives with hydroxyl groups in their radicals such as anhydrous ethanol, ethanol and methanol, among others.

More specifically, in the present invention, the organic solvent used was ethanol. However, those skilled in the art can foresee the use of any organic solvent with similar characteristics to ethyl alcohol as the extraction solvent in the present invention.

The above extraction process is conducted further with the aid of distilled water and under the control of reaction parameters, such as the use of solvent, temperature and development reaction time, as well as, the stability process employed in the drying process step.

For the present embodiment, the reaction temperature is maintained within the range of about 50° C. to about 100° C., for a reaction development period of approximately 20 to 50 minutes. For the present embodiment, the reaction temperature was maintained preferably at about 80° C. More specifically, the reaction temperature was maintained preferably at approximately 70° C. over a period of about 30 minutes and the selected procedure for the step of drying the extract as obtained was spray-dry, because this promotes a minimum degradation of the extract so as to ensure the stability and concentration of the natural chemical constituents of the extract.

These procedures provide the obtaining of an extract with controlled composition, necessary to establish the therapeutic properties of the herbal medicine intended for the disorders associated with the digestive tract which cause gastric mucosal lesions, such as peptic ulcer, gastritis, gastropathy, peptic ulcer disease and duodenitis in different stages.

Additionally, for the extraction process developed by the present invention, the step of drying the extract can also be accomplished by the technique of lyophilization, or by means of any other method known to those skilled in the art that can control the process, while avoiding decomposition or oxidation of the constituents present in said plant extract.

The hydroalcoholic extract of *Schinus terebinthifolius* obtained by controlled extraction process described herein, is the active ingredient of a pharmaceutical composition which is the object of this embodiment.

Additionally, in the scope of the present invention, there are substances isolated from said crude extract of *Schinus*, preferably from *Schinus terebinthifolius*, which also consist of active ingredients of pharmaceutical compositions of the present invention.

For purification and isolation of the analytical marker of hydroalcoholic extract from the bark of *Schinus terebinthifolius* was used High Performance Liquid Chromatography Preparative (HPLC-P) with C18 reverse phase columns and analytical grade solvents. We also used Spectroscopic techniques of Ultraviolet/Visible (UV/VIS), infrared (IR) and NMR $^1$H and $^{13}$C ($CD_3OD$) and mass spectrometry (MS) and MS-MS.

In the present invention, the major marker identified was Gallic Acid, one of the principle major constituents of the crude extract of *Schinus terebinthifolius*, and which alone shows better therapeutic activity in relation to disorders of the digestive tract, when combined with tannin.

Specifically, for the present embodiment, the chromatographic profile of this extract was determined by phytochemical research according to data presented in Tables below:

TABLE 1

Data analysis of chromatographic conditions of the analytical profile of hydroalcoholic extract of the stem bark of *Schinus terebinthifolius*.

| Sample | Hid Ext. Aroeira/Lot |
|---|---|
| Analytical Column | C18 |
| Solvent | $MeOH:H_2O$ - Gradient 5% - 100% B for 45 min |
| Output | 1.5 mL/min |
| $V_{injection}$ | 20 µL |
| Detector (UV) | 254 nm |

TABLE 2

Data analysis of chromatographic conditions of the
analytical profile of hydroalcoholic extract of the
stem bark of *Schinus terebinthifolius*.

| Sample | Hid Ext. Aroeira - INFAN/Lot |
|---|---|
| Analytical Column | C18 |
| Solvent | MeOH:H$_2$O - Gradient 5% - 100% B for 45 min |
| Output | 2.5 mL/min |
| V$_{injection}$ | 20 μL |
| Detector (UV) | 254 nm |

TABLE 3

Data analysis of chromatographic conditions of the
analytical profile of hydroalcoholic extract of the
stem bark of *Schinus terebinthifolius*.

| Sample | Hid Ext. Aroeira - INFAN/Lot |
|---|---|
| Analytical Column | C18 |
| Solvent | ACN:H$_2$0 Gradient 5% - 100% B for 60 min |
| Output | 2.0 mL/min |
| V$_{injection}$ | 20 μL |
| Detector (UV) | 254 nm |

TABLE 4

Data from GPC analysis of chromatographic peak
purity of the hydroalcoholic extract of the stem
bark of *Schinus terebinthifolius*.

| Sample | Hid Ext. Aroeira - INFAN/Lot |
|---|---|
| Analytical Column | Syneri 4u Hydro-RP 80 A. 250 × 4.6 mm |
| Solvent | Pump A: H$_2$O:HCOOH (99.9:0.1) |
| | Pump B: MeOH |
| Elution solvent | 10% to 25% MeOH in 25 min |
| Output | 1.0 mL/min |
| V$_{injection}$ | 5.0 ul |
| Detector (UV/VIS) | 254 nm |

TABLE 5

Data analysis of chromatographic conditions on the purity
of the chromatographic peak of the hydroalcoholic extract
of the stem bark of *Schinus terebinthifolius*.

| Sample | Hid Ext. Aroeira - INFAN/Lot |
|---|---|
| Analytical Column | Syneri 4u Hydro-RP 80 A. 250 × 4.6 mm |
| Solvent | Pump A: H$_2$O:HCOOH (99.9:0.1) |
| | Pump B: MeOH |
| Elution solvent | 10% to 25% MeOH in 25 min |
| Output | 1.0 mL/min |
| V$_{injection}$ | 5.0 ul |
| Detector (UV/VIS) | 280 nm |

The pharmaceutical composition described herein, comprising a pharmacologically active amount of the hydroalcoholic extract, already obtained, and at least one pharmaceutically acceptable carrier.

Additionally, a second pharmaceutical composition, also an object of the present embodiment, comprises a pharmacologically active amount of at least one substance isolated from crude hydroalcoholic extract, obtained herein, and at least one pharmaceutically acceptable carrier. More specifically, in the present embodiment, one of the possible obtained pharmaceutical compositions comprising a pharmacologically active amount of gallic acid and a pharmaceutically effective vehicle.

For the present embodiment, the pharmaceutically acceptable are selected from, non-toxic and inactive excipient substances, such as diluents, wetting agents, colors, adsorbents, binders, disintegrants, buffers, sweeteners, lubricants, dissolution modulators and flow promoters, used for modulating the bioavailability and for greater production.

More specifically, the excipients of the group of diluents may be selected from among the soluble and insoluble diluents, particularly lactose, sucrose, mannitol and derivatives; lactate, starch, microcrystalline cellulose, calcium phosphate, or any other substance with characteristics similar to those described above.

The excipients from the group of adsorbents are used to fix volatile products and to absorb water. They protect hydrolysable or hydroscopic pharmaceuticals and can be selected from among substances derived from silica or any other substance with similar characteristics to those described above.

More specifically, the binders are selected from the group of sugars such as sucrose, glucose, lactose, or, PVP, amide paste and some polysaccharides such as acacia and gum arabic.

The use of the excipients from the group of disintegrants is intended to accelerate the disintegration of the dosage form, sometimes compressed in water. For the present invention, these can be selected from among starch, lactose, croscarmellose sodium, sugar derivatives such as mannitol, isomatol, sorbitol and others.

More specifically, the excipients from the group of lubricants that may be used are selected from Mg and Ca stearates, polyethylene glycol (PEG), talc and aerosil, or any other substance with similar characteristics to the substances described above.

More specifically, the excipients from the wetting group that can be used are selected from among surfactants such as sodium lauryl sulfate, tween, or any other substance with similar characteristics to the substances described above.

More specifically, the excipients from the buffer group which can be used are selected from magnesium carbonate, alkaline phosphates and carbonates of calcium and sodium, or even any other substance with similar characteristics to the substances described above.

Sweeteners are selected from sugars and derivatives thereof, such as sodium saccharine and aspartame, and are intended to add flavor to oral dosage forms, such as buccal and sublingual tablets.

It should be emphasized that the invention is not limited to the above described substances. A person with knowledge of the technique is able to replace any of the substances described above, equivalent to another substance, since that substance has functional characteristics similar to that which it will replace.

In a preferred embodiment of the invention, said pharmaceutical composition comprises a mixture of the hydroalcoholic extract in proportions of ethanol:water 50:50 to 95:05. However, the ratio of ethanol:water of 75:25 is preferably used. More preferably, the ratio of ethanol:water used is 60:40.

For the present embodiment, these compositions are used in the preparation of medications for prophylaxis and/or treatment of disorders associated with the digestive tract.

Following definitions shall apply to disorders of the digestive tract: peptic ulcer, gastritis, gastropathy, duodenitis, inflammation caused by *H. pylori*, among others.

More particularly, these drugs are delivered through the oral route with their acceptable dosage forms being tablets, pills, capsules, solutions or suspensions.

In a preferred embodiment of the invention said pharmaceutical compositions are in tablet form. Such tablets may or may not be coated.

In the case of a coated tablet, such coating is preferably promoted by a polymer based on cellulose. Preferably, but not limited to this option to the present invention, the microcrystalline cellulose was used as a coating due to its multifunctional characteristics. Specifically, for the present invention, said tablet comprises at least one coated layer.

In a preferred embodiment of the present invention, each tablet comprises a total concentration of 233.60 mg, consisting of the extract of S. terebinthifolius (8.207 ml), microcrystalline cellulose, croscarmellose sodium and magnesium stearate.

In another preferred embodiment of the present invention, each tablet comprises a total concentration of 233.60 mg, consisting of about 1.60 mg gallic acid, microcrystalline cellulose, croscarmellose sodium and magnesium stearate.

Said tablet is typically identified by being coated, having an oval biconcave shape, being unscored, and having no reddish coloration.

It should be noted that such characteristics, as well as the excipients contained in said tablet, are common to those with knowledge in the art and therefore do not limit the aspects characterized by the present invention.

The pharmacological properties of the said tablet may be preserved for a period of about 24 months when stored away from light and moisture, at a temperature variation of between about 15 and 30° C. These are the parameters that characterize appropriate storage conditions.

A third objective of this invention is the use of said pharmaceutical compositions in the preparation of the class of herbal medicines for the prophylaxis and/or treatment of disorders associated with the digestive tract such as peptic ulcer, gastritis, and duodenitis gastropathies at different stages, with posology and daily dosing.

The goal of treatment is to improve the quality of life of patients by providing rapid relief of symptoms and reducing tissue damage in the mucosa. Therefore, it is noteworthy that the efficacy of treatment is the potential complete relief of symptoms of gastritis, especially the common symptoms such as epigastric pain, heartburn, nausea and early satiety so typically present in this group of diseases.

The above described use of drugs by the present invention is indicated for patients in the amount of about 1 to about 4 tablets per day. More particularly, the recommended daily dose is 1 to 2 tablets per day.

In a preferred embodiment of the invention, each tablet of medication, developed from the extract of S. terebinthifolius, comprises approximately 6.00 mL to approximately 10.00 mL of said hydroalcoholic extract. More specifically, said medication comprises from approximately 7.00 mL to 9.00 mL of hydroalcoholic extract. More particularly, in one preferred embodiment of the invention, said medication comprises approximately 8.207 ml of said hydroalcoholic extract of S. terebinthifolius.

In a preferred embodiment of the present invention, it can be considered that the proportion of gallic acid extract of S. terebinthifolius is about 0.05 mg/mL to about 0.5 mg/mL. More specifically, it can be considered that the proportion of gallic acid extract of S. terebinthifolius is about 0.1 mg/mL to about 0.4 mg/mL. Even more particularly, it can be considered that the proportion of gallic acid extract of S. terebinthifolius is approximately 0.2 mg/mL.

In another preferred embodiment of the invention, each tablet of medication, developed from gallic acid isolated from the extract of a plant of the Anacardiaceae family, particularly S. terebinthifolius, comprises about 0.01 to 5.0 mg/mLd of gallic acid. More specifically, each of the tablets of medication comprises between approximately 1.0 to 2.0 mg/ml gallic acid. More specifically, the tablet of the present invention comprises about 1.6 mg/ml gallic acid.

In order that the invention may be better understood, the following is detailed in the form of examples. However, the examples described herein have a purely illustrative character and do not limit the forms of the invention.

Example 1: Patient Selection

To evaluate the efficacy of hydroalcoholic extract of S. terebinthifolius in the form of a medication, 72 volunteer patients of both genders with diagnosed gastritis were selected. Anthropomorphic characteristics, such as age, weight and height were similar. The criteria for inclusion of patients in the sample were aged between 16 and 80 years (mean age was 40 years), with diagnosis of gastritis confirmed by endoscopy and pathological examination, and consent after clarification for study participation. We excluded patients who were treated with proton pump inhibitors, anti-inflammatory non-steroidal, H-2 receptor blockers and/or antacids during the month preceding the study.

Patients included in the sample performed two esophagogastroduodenoscopy tests (EGD) with biopsy and analysis for Helicobacter pylori. The first test was made before the treatment, and the second, after four weeks (28 days) on medication.

The sample was randomly divided into two groups:
Group I—38 patients who used the medication based on Aroeira (Schinus terebinthifolius Raddi);
Group II—34 patients who used the drug Omeprazole (control group).

The protocol for administration of medications included: ingestion of one (1) the tablet based on Aroeira (about 233.60 mg) twice daily for four weeks (28 days), or the ingestion of 20 mg Omeprazole, two tablets twice daily for the same period.

Classification with gradations and intensity of gastritis was based on the Sydney System.

Example 2: Method of Analysis of Results

For data analysis, we used the Epi Info program, v.3.5.1, and Microsoft Excel 2007. Since they are categorical variables, Odds Ratios were evaluated and significant results were verified through a crude chi-squared test or with a Yates correction, when applicable, and alternatively the Fisher Exact Test when indicated. A Z test was also used to compare proportions when the expected frequencies were greater than or equal to 5. Confidence intervals were calculated for 95% confidence, with significant differences smaller than 5%.

Results

The results were obtained through a questionnaire completed by each patient, under the supervision of a specialist.

In the analysis of the questionnaire that the patients were given before and after treatment, it was found that those treated with Aroeira showed an improved percentage of nausea, heartburn and epigastric pain higher then when compared to those treated with Omeprazole.

Regarding abdominal discomfort relieved with meals, two drugs, Aroeira and Omeprazole were similar (Table 6).

According to statistical analysis, there was no significant difference (at 5%) in the proportion of patients who saw improvement with the use of medicines.

Comparing the results, it was found that the proportion of patients treated with Aroeira reported a reduction in the sensation of nausea, heartburn and epigastric pain, respectively, of 1.2, 1.1 and 1.2 times greater than the group treated with Omeprazole.

Finally, with regard to abdominal discomfort relieved with meals, there was no difference in the proportions of the two groups.

TABLE 6

Percentage of improvement in symptoms after treatment

| Study Variables | Type of Treatment | | Statistics | |
|---|---|---|---|---|
| | Aroeira | Omeprazole | Z Test | Significance |
| Nausea | 86.40 | 72.20 | 1.112 | 0.13299 |
| Heartburn | 79.40 | 71.40 | 0.77 | 0.22083 |
| Frequent epigastric pain | 84.40 | 72.70 | 1.04 | 0.14819 |
| Abdominal discomfort relieved with meals | 85.70 | 85.70 | 0.00 | 0.50000 |

Figure 1:
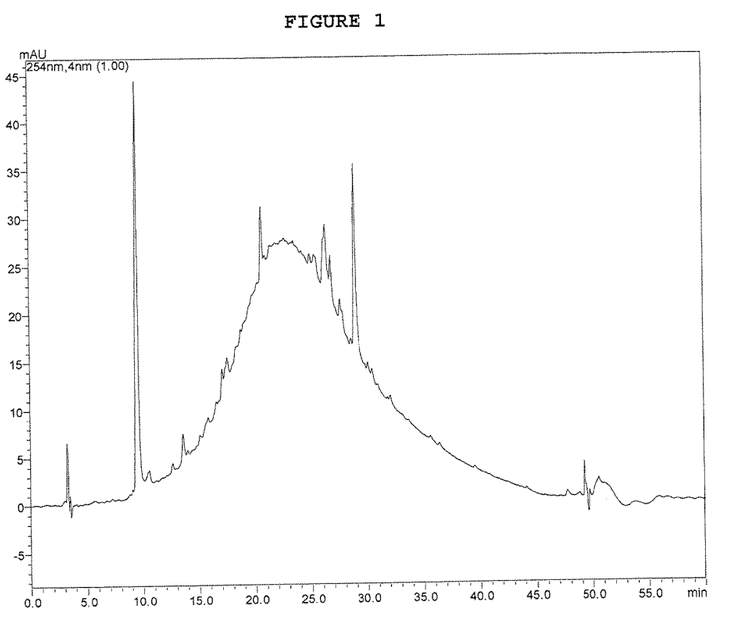
FIG. 1 shows a chromatogram (HPLC) of the hydroalcoholic extract of the stem bark of *Schinus terebinthifolius* in the conditions specified in Table 1.
Figure 2:
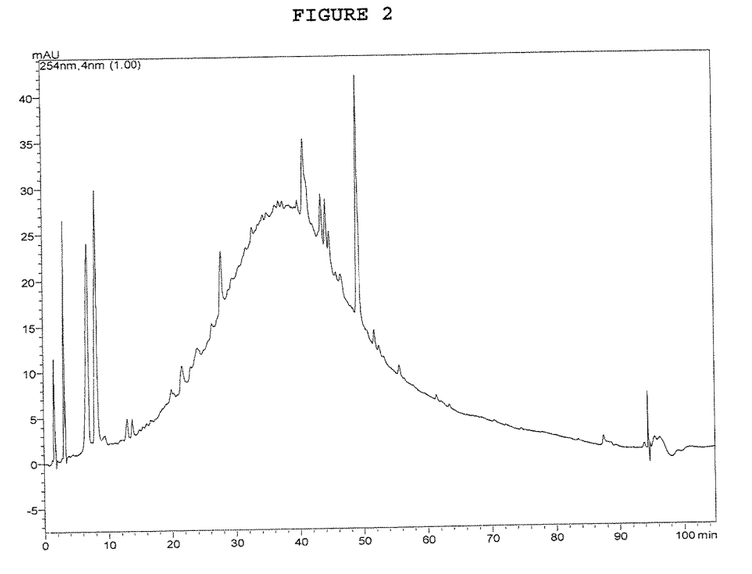
FIG. 2 shows a chromatogram (HPLC) of the hydroalcoholic extract of the stem bark of *Schinus terebinthifolius* obtained under the conditions specified in Table 2.
Figure 3:
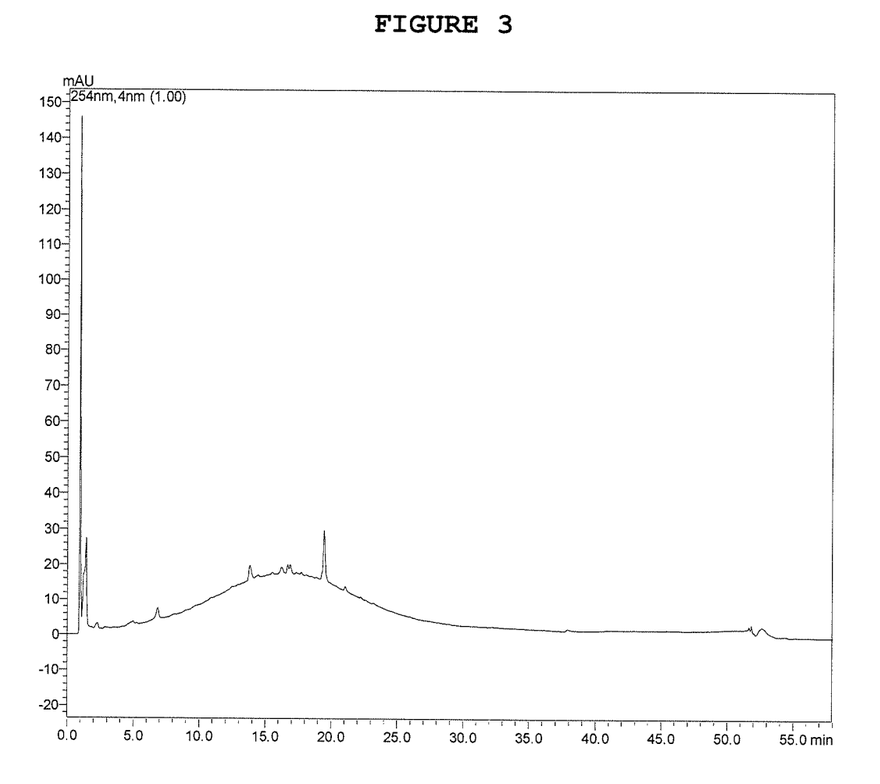
FIG. 3 shows a chromatogram (HPLC) of the hydroalcoholic extract of the stem bark of *Schinus terebinthifolius* in the conditions specified in Table 3.
Figure 4:
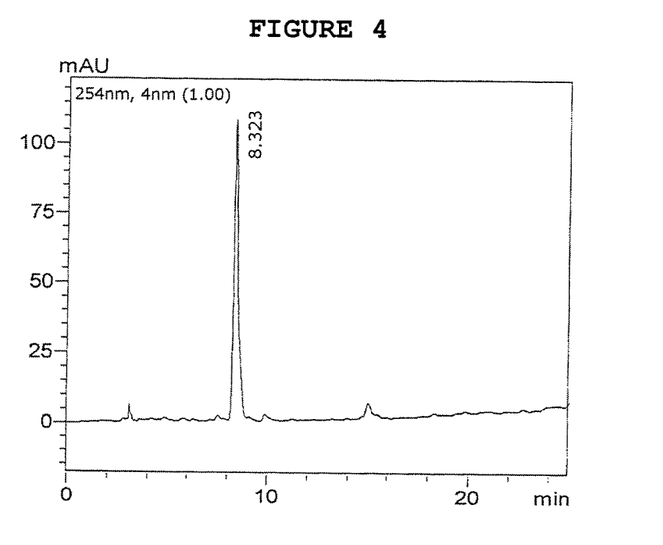
FIG. 4 shows a chromatogram (HPLC) of the hydroalcoholic extract of the stem bark of *Schinus terebinthifolius* peaking in Tr 8.32 min, chromatographic conditions presented in Table 4 (Detector UV/VIS 254 nm).
Figure 5:
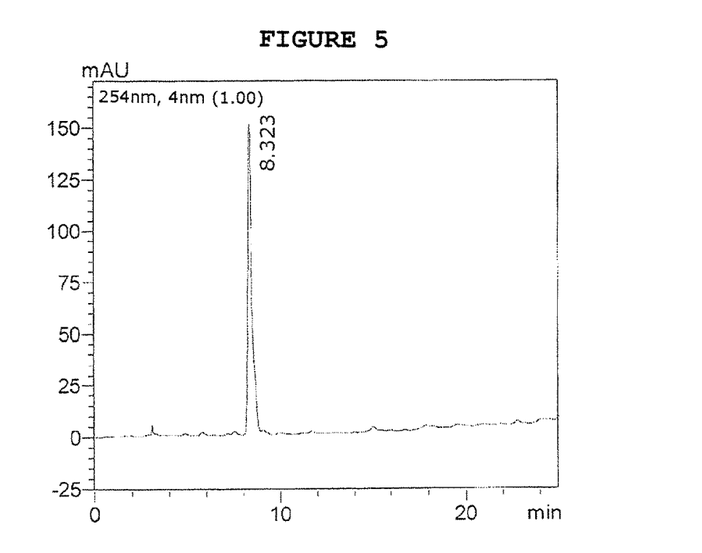
FIG. 5 shows a chromatogram (HPLC) of the hydroalcoholic extract of the stem bark of *Schinus terebinthifolius* peaking in Tr 8.32 min, chromatographic conditions presented in Table 5 (Detector UV/VIS 280 nm).
Figure 6:
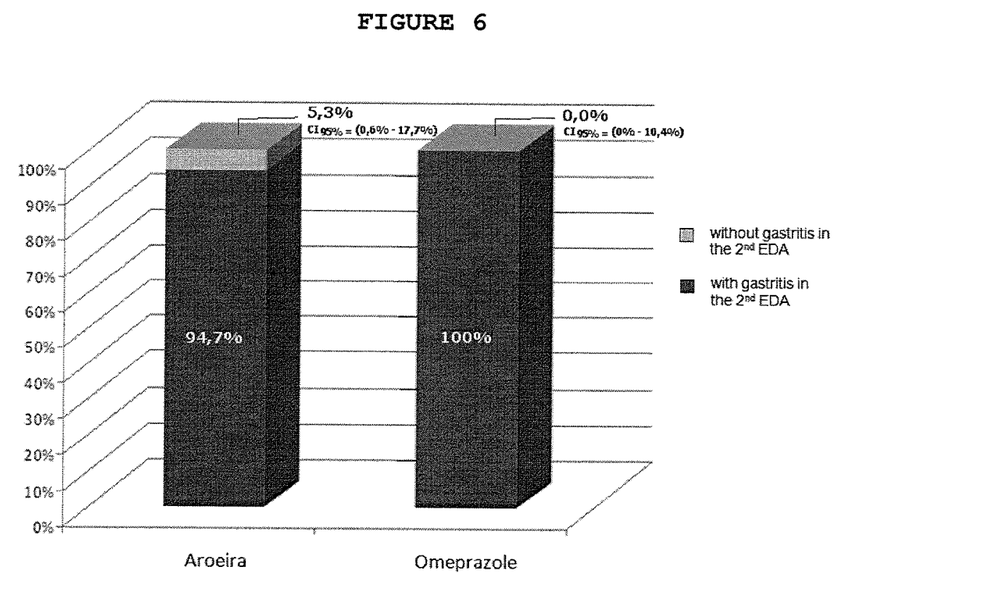
FIG. 6 shows the graphic distribution of improvement in the 2nd EDA findings in patients treated with Omeprazole compared to Aroeira. The clear portion of the graph shows the ratio of patients without gastritis in the 2nd EDA, while the dark part of the graph shows the ratio of patients with gastritis in the 2nd EDA.

Comparing the upper gastrointestinal endoscopies (EGD) performed before and after treatment, it was observed that 5.3% (0.6<CI<17.7) of patients treated with Aroeira showed disappearance of endoscopic mucosal injury in the 2nd endoscopy. But there was no statistically significant difference in the result reached by the group treated with Omeprazole, as shown in FIG. 6 and Table 7.

When the improvement of symptoms associated with gastritis after treatment were analyzed, there was no significant difference between patients submitted to both treatments, with a 5% level of confidence, as shown in Table 7.

Regarding the eradication rate of *H. pylori* following treatment with the two drugs, it is clear that patients treated with Aroeira have a higher cure rate than those treated with Omeprazole (17.1% versus 9.4%, respectively).

Regarding the intensity of gastritis, it was found that 64.3% of patients treated with Aroeira, initially diagnosed with moderate gastritis, showed significant improvement, and this percentage is 2.3 times higher than those treated with Omeprazole.

Moreover, 35% of patients who had an initial diagnosis of mild or discrete gastritis, who were treated with Aroeira, progressed to moderate gastritis, while 45.5% of those treated with Omeprazole had the same negative trend, as shown in Table 9, with the difference between results being assigned to chance. There was also no evidence of association between the two therapies or changes of the intensity of gastritis after treatment.

TABLE 7

Results of patients treated with Aroeira and Omeprazole, who presented with gastritis after treatment.

| Treatment | Exam Results | | | | Relative Risk IC 95% | Statistics | Significance |
|---|---|---|---|---|---|---|---|
| | Present | | Absent | | | | |
| | N° | % | N° | % | | | |
| *Gastritis* | | | | | | | |
| Aroeira | 36 | 94.74 | 2 | 5.26 | 0.95 0.88 < RR <1.02 | $\chi^2_{MH}$ 1.82 | 0.1779 |
| Omeprazol | 34 | 100 | 0 | 0 | | | |
| *H. pylori* | | | | | | | |
| Aroeira | 29 | 82.86 | 6 | 17.14 | | Z 0.93 | 0.35167313 |
| Omeprazole | 29 | 90.63 | 3 | 9.38 | | | |

TABLE 8

Results of patients treated with Aroeira and Omeprazole who showed *H. pylori* positive after treatment.

| Treatment | Results of Examination | | | | Relative Risk 95% | Statistics | Significance |
|---|---|---|---|---|---|---|---|
| | Present | | Absent | | | | |
| | No. | % | N | % | | | |
| *H. pylori* | | | | | | | |
| Aroeira | | 82.86 | 6 | 17.14 | | Z 0.93 | 0.35167313 |
| Omeprazole | | 90.63 | | 9.38 | | | |

Comparison of intesity levels of gastritis by means of histopathological examination before and after treatment.

| Intensity before Treatment | Intensity after Treatment | | | | OR IC 95% | $\chi^2$ p-value |
|---|---|---|---|---|---|---|
| | Mild/Discrete | | Moderate | | | |
| | No. | % | N | % | | |
| *Mild/Discrete* | | | | | | |
| Aroeira | 13 | 65.00 | 7 | 35.00 | 1.55 0.45 < OR <5.37 | 0.48 |
| Omeprazole | 12 | 54.50 | 10 | 45.50 | | 0.49058 |
| *Moderate* | | | | | | |
| Aroeira | 9 | 64.29 | 4 | 30.77 | 6.00 1.02 < OR <35.37 | 4.20 |
| Omeprazole | | 27.30 | 8 | 72.70 | | 0.04053 |

When all the results are analyzed, it is evident that Aroeira, i.e. the medication based on Aroeira, improved symptoms associated with gastritis with significantly more efficacy than Omeprazole, which was used as the reference drug in these cases.

It has been observed that patients with chronic gastritis, and mucosal injury with associated dyspeptic symptoms, responded more favorably to treatment with the oral Aroeira than with Omeprazole, administered as control, in therapeutic doses of 20 mg twice a day.

Data from this trial also indicate a likely anti *H. pylori* action associated with Aroeira.

Regarding the intensity of gastritis, using the Sydney classification, 64.3% of patients treated with Aroeira initially diagnosed with "mild gastritis" showed significant improvement, and this percentage was 2.3 times higher than those treated with Omeprazole.

The invention claimed is:

1. A method for treating an *H. pylori*-effected disorder associated with the digestive tract comprising administering to a subject suffering therefrom an herbal medicine comprising an effective amount of a plant extract obtained from the species *Schinus terebinthifolius*, wherein the extract is obtained by an extraction reaction conducted with an organic solvent comprising alcohol and water, and wherein said extract of *Schinus terebinthifolius* is obtained from stem bark.

2. The method according to claim 1, wherein the extract in the administered herbal medicine has a therapeutic activity on gastric mucosal lesions in the subject.

3. The method according to claim 2, wherein the gastric mucosal lesions are selected from the group consisting of peptic ulcers, gastritis, gastropathy, peptic ulcer disease, inflammation, and duodenitis in different stages.

4. The method according to claim 1, wherein said extract is *Schinus terebinthifolius* Raddi.

5. The method according to claim 1, wherein the alcohol is selected from the group consisting of ethanol and methanol.

6. The method according to claim 5, wherein the organic solvent is ethanol and the extract is obtained at a reaction temperature between about 50° C. to about 100° C. for a period of development of the reaction from approximately 20 to 50 minutes.

7. The method according to claim 6, wherein the reaction temperature is approximately 70° C. for a period of about 30 minutes and the extract is dried by a method selected from the group consisting of spray drying and lyophilization.

8. The method according to claim 1, wherein said herbal medicine is administered orally.

9. The method according to claim 8, wherein the herbal medicine is in a form selected from the group consisting of tablets, pills, capsules, solutions and suspensions.

10. The method according to claim 9, wherein the herbal medicine form is a tablet.

11. The method according to claim 10, wherein said tablet is a coated tablet.

12. The method according to claim 11, wherein the tablet comprises at least one coated layer formed by a cellulosic polymer.

13. The method according to claim 12, wherein the tablet has a total mass of 233.60 mg, consisting of a hydroalcoholic extract of *S. terebinthifolius*, microcrystalline cellulose, croscarmellose sodium and magnesium stearate.

14. The method according to claim 13, wherein the tablet comprises approximately 6.00 mL to about 10.00 mL of said hydroalcoholic extract.

15. The method according to claim 14, wherein said tablet comprises from about 7.00 mL to about 9.00 mL of said hydroalcoholic extract.

16. The method according to claim 14, wherein said tablet comprises about 8.207 mL of said hydroalcoholic extract of *S. terebinthifolius*.

17. The method according to claim 10, wherein 1 to 4 of said tablets are administered to the subject per day.

* * * * *

UNITED STATES PATENT AND TRADEMARK OFFICE
CERTIFICATE OF CORRECTION

PATENT NO. : 10,383,909 B2
APPLICATION NO. : 13/816469
DATED : August 20, 2019
INVENTOR(S) : Avaniel Marinho Da Silva et al.

It is certified that error appears in the above-identified patent and that said Letters Patent is hereby corrected as shown below:

On the Title Page

(75) The third inventor's name reads:
Severno Barbosa DOS SANTOS

Should read:
Severino Barbosa DOS SANTOS

Signed and Sealed this
Eighth Day of October, 2019

Andrei Iancu
*Director of the United States Patent and Trademark Office*